United States Patent
Chapal et al.

(10) Patent No.: US 10,028,970 B2
(45) Date of Patent: Jul. 24, 2018

(54) COMPOSITION COMPRISING CASHEW APPLE EXTRACT

(75) Inventors: Nicolas Chapal, Combaillaux (FR); Max Reynes, Clapiers (FR); Vickram Beejmohun, Montpellier (FR); Manuel Dornier, Clapiers (FR)

(73) Assignee: NATUREX, Avignon (FR)

( * ) Notice: Subject to any disclaimer, the term of this patent is extended or adjusted under 35 U.S.C. 154(b) by 502 days.

(21) Appl. No.: 14/124,208

(22) PCT Filed: Jun. 7, 2012

(86) PCT No.: PCT/EP2012/060822
§ 371 (c)(1),
(2), (4) Date: Dec. 5, 2013

(87) PCT Pub. No.: WO2012/168381
PCT Pub. Date: Dec. 13, 2012

(65) Prior Publication Data
US 2014/0100177 A1 Apr. 10, 2014

(30) Foreign Application Priority Data
Jun. 7, 2011 (EP) .................................... 11305699

(51) Int. Cl.
A61K 36/22 (2006.01)
A61K 31/7028 (2006.01)
A61K 31/352 (2006.01)
A23L 33/105 (2016.01)

(52) U.S. Cl.
CPC ........ *A61K 31/7028* (2013.01); *A23L 33/105* (2016.08); *A61K 31/352* (2013.01); *A61K 36/22* (2013.01); *A61K 2236/39* (2013.01)

(58) Field of Classification Search
CPC ....................................................... A61K 36/22
USPC .................................. 424/769, 776, 777, 725
See application file for complete search history.

(56) References Cited

U.S. PATENT DOCUMENTS

| | | | |
|---|---|---|---|
| 2008/0171707 A1 | 7/2008 | Amiot-Carlin et al. | |
| 2011/0263698 A1* | 10/2011 | Nagamine ............. | A23L 1/3002 514/456 |
| 2013/0216636 A1* | 8/2013 | Florence ................. | A61K 8/97 424/777 |

FOREIGN PATENT DOCUMENTS

| | | | |
|---|---|---|---|
| JP | 2008-533113 A | | 8/2008 |
| JP | 2009-155259 | * | 7/2009 |
| JP | 2010-525051 A | | 7/2010 |
| WO | WO 2006/014028 A1 | | 2/2006 |
| WO | WO 2006/103514 A1 | | 10/2006 |
| WO | WO 2009/027849 A2 | | 3/2009 |
| WO | WO 2010/073757 | * | 7/2010 |

OTHER PUBLICATIONS

Abreu et al., "Bioactive Compounds and Antioxidant Activity of Cashew Apple (*Anacardium occidentale* L.) from Commercial Early Dwarf Clones", Acta Hort., vol. 841, 2009, pp. 451-454, XP008141847.
Brito et al., "Determination of the flavonoid components of cashew apple (*Anacardium occidentale*) by LC-DAD-ESI/MS", Food Chemistry, vol. 105, 2007, pp. 1112-1118, XP002657648.
International Search Report for International Application No. PCT/EP2012/060822 dated Sep. 4, 2012.
Michodjehoun-Mestres et al., "Isolation, Characterization, and Determination of 1-O-trans-Cinnamoyl-β-D-glucopyranose in the Epidermis and Flesh of Developing Cashew Apple (*Anacardium occidentale*) and . . . ", J. Agric. Food Chem., vol. 57, 2009, pp. 1377-1382, XP002657650.
Michodjehoun-Mestres et al., Monomeric phenols of cashew apple (*Anacardium occidentale* L.), Food Chemistry, vol. 112, 2009, pp. 851-857, XP002657649.
Satyanarayana et al., "Studies on the polyphenols of cashew apple (*Anacardium occidentale*)", Leather Science, vol. 25, 1978, pp. 51-54, XP008141848.
WPI, Accession No. 2009-L62987, Thompson Scientific, Jul. 16, 2009, 2 pages, XP002657647.

* cited by examiner

*Primary Examiner* — Chris R Tate
(74) *Attorney, Agent, or Firm* — Birch, Stewart, Kolasch & Birch, LLP

(57) ABSTRACT

The invention concerns a cashew apple extract and a composition comprising a cashew apple extract and optionally a carrier, in particular for use for allowing reduction of body weight gain or limitation of increasing body weight, reduction or limitation of fat storage, of fatty liver, of liver triglycerides level, of hypertriglyceridemia, of glycemia level, of insulinemia, of insulin resistance, and/or of one or several factors of metabolic syndrome.

12 Claims, 9 Drawing Sheets

(Alcoholic: p<0.01 from Day 4; Aqueous: p<0.05 from day 46)

(**p<0.01)

(*p<0.05 ; **p<0.01)

(*p<0.05)

COMPOSITION COMPRISING CASHEW APPLE EXTRACT

The present invention relates to an extract for allowing reduction or control of body weight or limitation of body weight gain, reduction or limitation of increase of fat storage, of fatty liver, of liver triglycerides level, of hypertriglyceridemia, of glycemia level, of insulinemia level, of insulin resistance, and/or of different factors of metabolic syndrome, and to a composition comprising such an extract.

More particularly, the extract may exhibit an action on risk factor(s) which may have an impact on fatty cirrhosis, cardiovascular disease, diabetes complications and/or diabetes. Among these risk factors, may be cited the overweight, in particular obesity, the increasing of fat storage, of fatty liver, of liver triglycerides level, of hypertriglyceridemia, of glycemia level, of insulinemia level, of insulin resistance and/or of different factors of metabolic syndrome.

The invention concerns also food or dietary supplement comprising such an extract.

The invention also relates to a composition for use for prevention or treatment of one or several factors of metabolic syndrome, obesity, fatty cirrhosis, cardiovascular disease, diabetes complications and/or diabetes.

The modern society leads more and more to the increase of risk factors of diseases such as fatty cirrhosis, cardiovascular disease, diabetes complications and/or diabetes.

The known compounds or compositions which may be used to treat these diseases and/or to limit one or several of their risk factors, in particular the reduction of body weight, may be insufficiently efficient, too expensive, exhibiting undesired side effects, having insufficient organoleptic qualities, they may change the colour, taste, and/or aspect of the food it is intended to be combined with, difficult to introduce into food, at least with some types of food, insufficiently stable, may present a low solubility, may be insufficiently versatile, may present a sourcing not stable enough, and/or abundant, or they may come from a precursor or precursors which may have other uses.

On the other hand the diets for regulating body weight often have a limited success. Low caloric diets for example may cause a temporary loss of body weight but have not proven their efficiency on the long term for people wanting to lose weight and to maintain a defined weight.

In the continued search of effective anti-obesity agents, medicinal plants have been screened to find new compounds with pancreatic lipase inhibitory activity.

Medicinal plants have been used as dietary supplements for body weight management and control in many countries. In this sense, presence of pancreatic lipase inhibitors has been demonstrated in different plant species, although more research is needed for identifying and characterizing effective lipase inhibitors. Lipase inhibitors of plant origin include certain proteins, such as those from soybean and from wheat bran and germ. Other proteins that strongly inhibit hydrolysis of triglycerides are the basic protein protamine and $\epsilon$-polylysine, which could act, as several amphiphilic proteins like ovoalbumin and $\beta$-lactoglobulin, by the desorption of lipase from its substrate due to a change in interfacial quality.

As cited in JP 2009-155259, apple cashew also may harbour lipase inhibitor activity.

The invention thus aims to solve all or part of the above cited problems.

According to an aspect, the invention has for subject matter a cashew apple extract.

Among the advantages of the invention is the fact that it allows the use of a product which is until now not used at all, or at least which has very few uses, and at the same time easily collected, in particular as it may be collected at the same time than the cashew nuts.

According to another aspect, the invention has for subject matter a composition comprising, or consisting of, a cashew apple extract, and optionally a carrier.

The extract or the composition may be intended for use in a curative or in a preventive treatment for reduction or control of body weight or limitation of body weight gain, reduction or limitation of increasing of fat storage, of fatty liver, of liver triglycerides level, of hypertriglyceridemia, of glycemia level, of insulinemia, of insulin resistance, and/or of different factors of metabolic syndrome.

The invention also has for subject matter a food composition, solid or liquid, comprising a cashew apple extract, and optionally a carrier.

The invention also has for subject matter a dietary or food supplement or a nutraceutical or food composition comprising, or consisting of, a cashew apple extract, and optionally a carrier, in particular for allowing reduction of body weight or limitation of body weight gain, reduction or limitation of increasing of fat storage, of fatty liver, of liver triglycerides level, of hypertriglyceridemia, of glycemia level, of insulinemia, of insulin resistance, and/or of one, several or all the factors of metabolic syndrome.

According to another aspect, the invention has for subject matter a pharmaceutical composition comprising, or consisting of, a cashew apple extract, in particular for use for preventing and/or treating fatty cirrhosis, cardiovascular disease, diabetes complications and/or diabetes and/or one or several factors of metabolic syndrome, for example high level of insulin, hypercholesterolimia, hypertension, overweight, in particular obesity, and hyperglycemia.

The composition may be for use for modulating body weight of a subject, in particular losing, controlling or helping to control the body weight of a subject. The extract of the invention, or the composition according to the invention may be used for preventing obesity in a subject in need thereof, or for treating obesity in a subject in need thereof.

In the instant description a subject may be human or animal, and in particular mammal.

According to still another aspect, the invention has for subject matter the use of a cashew apple extract for the preparation of a medicament or of a pharmaceutical composition.

Following yet another aspect, the invention has for subject matter a diet, in particular for allowing reduction of body weight or limitation of body weight gain, limitation or reduction of fat storage, of fatty liver, of liver triglycerides level, of hypertriglyceridemia, of glycemia level, of insulinemia, of insulin resistance, and/or of different factors of metabolic syndrome, comprising the step of at least one daily taking of a composition comprising, or consisting of, a cashew apple extract.

Figure 1:
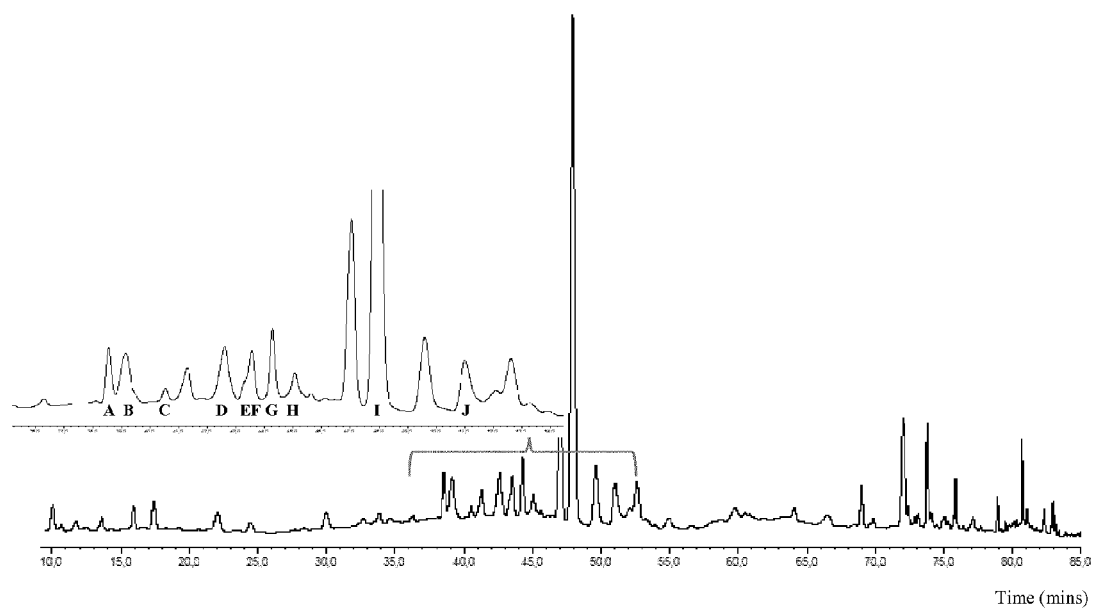
FIG. 1 presents analytical HPLC chromatograms of a hydro-alcoholic cashew apple extract at 280 nm.

The cashew apple extract may come from the total fruit, the skin and/or the flesh of the fruit, in particular the extract is from the total fruit. The extract according to the invention may be obtained from crude cashew apple, either from the entire fruit or from the remains of cashew apples used to obtain cashew apple juice, for example desiccated or frozen.

The expressions "weight of cashew apple extract" or "weight of extract" in the sense of the invention mean the dry weight of the cashew apple extract or the dry weight of the extract.

The extract may comprise an amount of organic compounds, in particular derivatives of cinnamic acid, quercetin and myricetin, of at least 2 g/kg, in particular at least 2.5 g/kg, and more particularly at least 3 g/kg, expressed in terms of the corresponding standards of cinnamic acid, quercetin and myricetin.

When the extract is an aqueous extract, it may comprise an amount of organic compounds, in particular cinnamic acid derivatives, quercetin derivatives and myricetin derivatives, of at least 2 g/kg, in particular at least 2.5 g/kg, and more particularly at least 3 g/kg expressed in terms of the corresponding standards cinnamic acid, quercetin and myricetin.

When the extract is an hydro-alcoholic extract, in particular with a water/ethanol 1/1 v/v, it may comprise an amount of organic compounds, in particular cinnamic acid derivatives, quercetin derivatives and myricetin derivatives, of at least 3.5 g/kg, in particular at least 4 g/kg, more particularly at least 4.5 g/kg, and still more particularly at least 5 g/kg, expressed in terms of the corresponding standards of cinnamic acid, quercetin and myricetin. The extract may comprise an amount of organic compounds, in particular cinnamic acid derivatives, quercetin derivatives and myricetin derivatives, ranging from 2 to 15 g/kg, in particular from 2.5 to 10 g/kg, and more particularly from 3 to 7 g/kg, expressed in terms of the corresponding standards of cinnamic acid, quercetin and myricetin.

The extract may comprise from 2 to 15 g/kg, in particular from 2.5 to 10 g/kg, and more particularly from 3 to 7 g/kg of cinnamic acid derivatives, quercetin derivatives and myricetin derivatives, expressed in terms of the corresponding standards of cinnamic acid, quercetin and myricetin.

When the extract is an aqueous extract, it may comprise an amount of organic compounds, in particular cinnamic acid derivatives, quercetin derivatives and myricetin derivatives, from 2 to 8 g/kg, in particular from 2.5 to 6 g/kg, and more particularly from 3 to 5 g/kg expressed in terms of the corresponding standards of cinnamic acid, quercetin and myricetin.

When the extract is an hydro-alcoholic extract, in particular with water/ethanol 1:1 v/v, it may comprise an amount of organic compounds, in particular cinnamic acid derivatives, quercetin derivatives and myricetin derivatives, from 3.5 to 15 g/kg, in particular from 4.5 to 10 g/kg, and more particularly from 5 to 7 g/kg, expressed in terms of the corresponding standards of cinnamic acid, quercetin and myricetin.

By "organic acids" is meant chemical substances found in plants, characterized by the presence of at least one carboxylic acid group per molecule and at least one aromatic part. Among organic acids may be cited cinnamic acid and its derivatives.

The amount of organic compounds may be determined using cinnamic acid, and flavonoids, in particular quercetin and myricetin, as standards, such as shown in the examples.

The amount of flavonoids may be determined using flavonoids, in particular quercetin and myricetin, as standards, such as shown in the Examples.

In other word, the amount of flavonoids is the weight of flavonoid in particular quercetin derivatives and myricetin derivatives, expressed in terms of the corresponding standards of quercetin and myricetin, determined as shown in the examples.

The amount of organic acids may be determined using cinnamic acid as standard, such as shown in the examples.

In other word, the amount of organic acids is the weight of cinnamic acid derivatives, expressed in terms of the corresponding standard of cinnamic acid, as shown in the examples.

More particularly, the composition comprises organic compounds, such as organic acids and flavonoids, having a sugar part, such as galactoside, glucoside, arabino-pyranoside, xylo-pyranoside, arabino-furanoside, rhamnoside.

The extract may comprise myricetin derivatives, in particular chosen from myricetin 3-O-galactoside (Compound A), myricetin 3-O-glucoside (Compound B), myricetin 3-O-xylo-pyranoside (Compound C), myricetin 3-O-arabino-pyranoside (Compound D), myricetin 3-O-arabino-furanoside (Compound E) and/or myricetin 3-O-rhamnoside (Compound F).

The extract may comprise myricetin derivatives in an amount of at least 1 g/kg, in particular at least 1.4 g/kg, and more particularly at least 1.7 g/kg of extract, expressed in terms of the corresponding standard of myricetin.

The extract may comprise myricetin derivatives, in an amount ranging from 1 to 6 g/kg, in particular 1.4 to 5 g/kg, and more particularly 1.7 to 4 g/kg, expressed in terms of the corresponding standard of myricetin.

When the extract is an aqueous extract, it may comprise an amount of myricetin derivatives, of at least 1.1 g/kg, in particular at least 1.3 g/kg, and more particularly at least 1.5 g/kg and/or from 1.1 to 4 g/kg, in particular 1.3 to 3 g/kg, and more particularly 1.5 to 2.5 g/kg, expressed in terms of the corresponding standard of myricetin.

When the extract is an hydro-alcoholic extract, in particular with a water/ethanol 1/1 v/v, it may comprise an amount of myricetin derivatives, of at least 2 g/kg, in particular at least 2.2 g/kg, and more particularly at least 2.5 g/kg and/or from 2 to 4.2 g/kg, in particular 2.2 to 3.6 g/kg, and more particularly 2.5 to 3.2 g/kg, expressed in terms of the corresponding standard of myricetin.

The extract may comprise quercetin derivatives, in particular chosen from quercetin 3-O-galactoside (Compound G), quercetin 3-O-glucoside (Compound H), and/or quercetin 3-O-rhamnoside (Compound J).

The extract may comprise quercetin derivatives in an amount of at least 0.75 g/kg, in particular at least 0.9 g/kg, and more particularly at least 1.0 g/kg of extract, expressed in terms of the corresponding standard of quercetin.

The extract may comprise quercetin derivatives, in an amount ranging from 0.75 to 3.5 g/kg, in particular 0.9 to 3 g/kg, and more particularly 1 to 2.5 g/kg, expressed in terms of the corresponding standard of quercetin.

When the extract is an aqueous extract, it may comprise an amount of quercetin derivatives, of at least 1 g/kg, in particular at least 1.3 g/kg, and more particularly at least 1.5 g/kg and/or from 1.1 to 4 g/kg, in particular 1.3 to 3 g/kg, and more particularly 1.5 to 2.5 g/kg, expressed in terms of the corresponding standard of quercetin.

When the extract is an hydro-alcoholic extract, in particular with a water/ethanol 1/1 v/v, it may comprise an amount of quercetin derivatives, of at least 0.75 g/kg, in particular at least 0.9 g/kg, and more particularly at least 1 g/kg and/or from 0.75 to 3 g/kg, in particular 0.9 to 2.5 g/kg, and more particularly 1 to 2.1 g/kg, expressed in terms of the corresponding standard of quercetin.

The extract may comprise a weight ratio myricetin derivatives/quercetin derivatives, using respectively myricetin and quercetin as standards, of at least 1.

The extract may comprise cinnamic acid derivatives, in particular 1-O-trans-cinnamoyl-beta-D-glucopyranose (Compound I), also called 1-O-trans-cinnamoyl beta-D-glucoside.

The extract may comprise an amount of cinnamic acid derivatives of at least 0.3 g/kg, in particular at least 0.35 g/kg, and more particularly at least 0.4 g/kg of extract, expressed in terms of the corresponding standard of cinnamic acid.

The extract may comprise cinnamic acid derivatives in an amount ranging from 0.3 to 3 g/kg, in particular 0.35 to 2.5 g/kg, and more particularly 0.4 to 2 g/kg, expressed in terms of the corresponding standard of cinnamic acid.

When the extract is an aqueous extract, it may comprise an amount of cinnamic acid derivatives, of at least 0.3 g/kg, in particular at least 0.35 g/kg, and more particularly at least 0.4 g/kg and/or from 0.3 to 1.5 g/kg, in particular 0.35 to 1.1 g/kg, and more particularly 0.4 to 0.9 g/kg, expressed in terms of the corresponding standard of cinnamic acid.

When the extract is an hydro-alcoholic extract, in particular with a water/ethanol 1/1 v/v, it may comprise an amount of cinnamic acid derivatives, of at least 0.9 g/kg, in particular at least 1.1 g/kg, and more particularly at least 1.3 g/kg and/or from 0.9 to 3.1 g/kg, in particular 1.1 to 2.8 g/kg, and more particularly 1.3 to 2.5 g/kg, expressed in terms of the corresponding standard of cinnamic acid.

Preferably, when the extract is an hydro-alcoholic extract, in particular with a water/ethanol 1/1 v/v, it may comprise an amount of 1-O-trans-cinnamoyl-beta-D-glucopyranose (Compound I), at least of at least 0.9 g/kg, in particular at least 1.1 g/kg, and more particularly at least 1.3 g/kg and/or from 0.9 to 3.1 g/kg, in particular 1.1 to 2.8 g/kg, and more particularly 1.3 to 2.5 g/kg, expressed in terms of the corresponding standard of cinnamic acid.

The extract may comprise a total phenol content, using Folin-Ciocalteu method, ranging from 3 to 7% by weight total phenol content equivalent to gallic acid.

Thus, following an aspect, the invention concerns a composition comprising, or consisting of, a cashew apple extract, and optionally a carrier, in particular an edible carrier, and/or a flavour agent.

Following an embodiment, the composition comprises at least 10% by weight, more particularly at least 25% by weight, even more particularly at least 50% by weight, still more particularly at least 75% by weight of the extract compared to the total weight of the composition.

The composition may comprise an amount of cashew apple extract going from 10 to 99% by weight, more particularly from 25 to 95% by weight, even more particularly from 50 to 95% by weight, still more particularly from 75 to 95% by weight compared to the total weight of the composition.

The composition, in particular the pharmaceutical composition, the nutraceutical composition or the dietary or food supplement, may comprise, or consist of, a cashew apple extract, and optionally a carrier.

More particularly the extract is aqueous or hydro-alcoholic, in particular hydro-ethanolic. The extract may in particular be the extract obtained or obtainable via the method disclosed in this description.

The dietary or food supplement may comprise an amount of extract ranging from 1 to 100% by weight compared to the total weight of the supplement.

The nutraceutical or the food composition may comprise an amount of extract ranging from 0.1 to 5% by weight compared to the total weight of the composition.

The supplements or the nutraceutical or food composition may be a liquid, a solid or a powder.

The composition may be formulated in order to allow a daily uptake for humans ranging from 10 to 80 mg/kg, and in particular around 30 mg/kg.

The cashew apple extraction may be performed on the total fruit, or alternatively on the skin and/or on the flesh of the fruit.

The invention also concerns a method for extracting cashew apple which may comprise, or consists in:
1) contacting crushed cashew apples with 2 to 20 times their weight with an extraction solvent, in particular at a temperature above 25° C., more particularly above 35° C., and still more particularly of around 50° C.,
2) filtering out the solids and collecting the solvent extract,
3) optionally washing the wet solid by stirring with an extraction solvent,
4) optionally filtering the solids and collecting the solvent extract,
5) combining the solvent extracts and removing non-soluble residues,
6) evaporating the solvents, and
7) recovering the dry extract.

The cashew apple extract may be aqueous, alcoholic, organic solvent soluble in water or a mixture thereof. Among the organic solvent soluble in water may be cited acetone.

The solvent of the extraction process can be aqueous, alcoholic, organic solvent soluble in water or a combination thereof.

Suitable solvents may be chosen from water, methanol, ethanol, acetone, n-propanol, iso-propanol, 2-butanol, and combinations thereof.

More particularly the extraction solvent comprises at least 75%, at least 90%, more particularly at least 95%, and even more particularly at least 99% by weight compared to the total weight of the extraction solvent, and still more particularly consists of such solvent(s).

Following an embodiment, the extraction is performed with water and/or an alcoholic solvent, in particular ethanol.

In case of an extraction performed with water and alcohol (for an hydro-alcoholic extract), in particular ethanol, the volume ratio water/alcohol may range from 80/20 to 20/80, in particular form 70/30, to 30/70, more particularly from 60/40 to 40/60, and even more particularly be of around 50/50.

The percentage of alcohol, and in particular ethanol, used for extraction can have an impact on the yield and composition of the biologically active compounds.

The extraction may be done using about a solvent in the range of 2 to 20 times, in particular 5 to 15 times and more particularly around 10 times the weight of solids. The extraction may be done one or several time, in particular 2 to 4 times.

The extraction may be performed at a temperature ranging from 25 to 70° C., in particular from 40 to 60° C., and more particularly around 50° C.

The extraction may last from 1 to 5 hours, in particular around 2 hours, under stirring, for example mechanical or magnetic stirring.

The remaining solids may be filtered out, in particular through a filter bag, and the extracts may be combined.

The wet solids may be extracted another time by stirring with a solvent, in particular a hydroalcoholic mixture, with a volume from 1 to 100 times the weight of the dry solids, and a stirring for about 10 to 120 minutes further, preferably for about 10 to 60 minutes further.

The solids are collected and the extracts may be combined.

The different extraction solutions may be combined and left for decantation, filtered through filter paper or centrifugation to remove non-soluble residues.

The clear supernatants obtained may be concentrated to about 5% to 20% of their initial volume, for example using a concentrator, and/or may be treated with food grade alcohol, in particular ethanol, in a definite proportion, for example 2 times the concentrated volume, to remove any precipitate formed. This step may allow removing all or parts of undesired compounds, such as polysaccharides or water soluble proteins.

A powdered extract may be obtained by drying the concentrated extracts, for example using spray drier, oven at 50-80° C., or vacuum drier.

The dry extract is weighed (g) and the extraction yield is calculated by the formula:

Yield %=(weight of dry extract/weight freshly pressed cake of fruits)×100

More particularly, the cashew apple extract may be obtained by the process comprising the following steps:
1) contacting crushed and pressed cashew apples with 2 to 20 times, in particular around 10 times, their weight with an extraction solvent, in particular a mixture ethanol-water comprising at least 30% by volume of ethanol, and more particularly a mixture ethanol-water having a 1/1 volume ratio, and stirring, for example for 2 hours, in particular at a temperature above 25° C., more particularly above 35° C., and still more particularly of around 50° C.,
2) filtering out the solids and collecting the solvent extract,
3) washing the wet solid by stirring with an extraction solvent, in particular with a volume corresponding to 1 to 100 times the weight of the dry solids, for example for about 15 to 30 minutes,
4) filtering the solids and collecting the solvent extract,
5) combining the extraction solutions and decanting or filtering them to remove non-soluble residues,
6) evaporating the solvents, for example by staying in an oven at 50-80° C. dried, or under vacuum, for example with vacuum spray drying, thus leading to a pale yellow syrup, and the concentrate may be freezed for lyophilisation, and
7) recovering the dry extract.

In general, the yield of extraction is ranging from 2 to 7% by weight of extract compared to the total weight of freshly pressed cake, in particular from 3 to 6% by weight, and more particularly is around 4% by weight.

The cashew apple extracts can be prepared on a commercial scale by repeating the extraction process that lead to the isolation of the extract of interest.

Thus small-scale extraction procedure can be scaled up, with optionally additional steps of quality control included to ensure reproducible results for the resulting extracts.

Various extraction processes can be employed. Generally, the extract is obtained by contacting the solid cashew apple with a solvent with adequate mixing and for a period of time sufficient to ensure adequate exposure of the solid plant material to the solvent such that biologically active molecules present in the plant material can be taken up by the solvent.

The solvent extraction process may be selected from direct and continuous (counter-current) extraction types at room temperature or at higher temperature with polar and/or non-polar solvent(s). Adequate contact of the solvent with the plant material can be encouraged by shaking the suspension. The liquid fraction is then separated from the solid (insoluble) matter resulting in the generation of two fractions: a liquid fraction, which is the potential extract, and a solid fraction. Separation of the liquid and solid fractions can be achieved by one or more standard processes known to those skilled in art.

EXAMPLES

Example 1

Preparation of Cashew Apple Extracts (CAE-Aqueous and CAE-Alcoholic)

Materials and Methods

Cashew apples (8 kg) are first crushed and pressed (hydraulic press) to remove the juice. The cake residue left (1.2 kg) is used for the following extraction processes.

CAE-Alcoholic Extraction Process

The freshly pressed cake (350 g) is extracted with about 3.5 L of 50% ethanol/water (V/V) for 2 hours at 50° C., under mechanical agitation. At the end of the extraction period, the solids are filtered out through a filter bag (PE-25) and 3.3 L of the liquid extract is removed.

The wet solids may be extracted one more time by stirring with another 2 volume of ethanol 50% for about 15 to 30 min further.

The solids are again filtered out and the obtained extracts were combined together, left for decantation and filtered through filter paper to remove non-soluble residues.

The clear supernatant obtained, was concentrated under reduced pressure to about 15% of its initial volume and is then treated with food grade ethanol in a definite proportion (2V) to remove any precipitate formed. After solid-liquid separation, the concentrated extract was freeze and lyophilized to obtain a yellow powder (18.4 g) of cashew apple.

The composition of the extract is shown in Table 1

CAE-Aqueous Extraction Process

The freshly pressed cake (350 g) is extracted with about 3500 g of demineralized water for 2 hours at 90° C., under mechanical agitation. At the end of the extraction period, the solids are filtered out through a filter bag (PE-25) and 3500 g of the liquid extract is removed.

The wet solids may be extracted one more time by stirring with another 2 volume of demineralized water for about 15 to 30 min further.

The solids are again filtered out and the obtained extracts were combined together, left for decantation and filtered through filter paper to remove non-soluble residues.

The clear supernatant obtained, was concentrated under reduced pressure, freeze and lyophilized to obtain a pale yellow powder (15.4 g) of cashew apple.

The composition of the extract is shown in Table 1.

Analytical Methods

Quantification of the total phenols content using Folin-Ciocalteu method: The extract of cashew apple CAE-Aqueous and CAE-Alcoholic may comprise between 3 and 7% by weight total phenol content equivalent to gallic acid.

Characterization and Quantification of the Polyphenol Content by HPLC:

HPLC-DAD Analysis:

Analytical HPLC (Dionex) is set up as required. In this invention, the mobile phase used was 0.1% formic acid into 1000 ml high purity water (solvent A) and acetonitrile (solvent B), utilizing the following gradient over a total run of 96 minutes with a flow rate of 0.7 ml/min. The gradients points were for time 0.0 minutes—95% A and 5% B; for time 10 minutes—90% A and 10% B; held isocratic for 10 minutes and from 20 minutes to 40 minutes the gradient varied linearly from 10% to 20% B; again held isocratic for 10 minutes; from 50 minutes to 65 minutes the gradient varied linearly from 20% to 30% B and to 50% during the next 10 minutes; from 75 minutes to 76 minutes the gradient varied linearly from 50% to 100% B and was held isocratic for 10 minutes. Back to original conditions of 95% A and 5% B from 85 minutes to 86 minutes and held isocratic for 10 minutes. Phenolic compounds in the eluent was detected with a UV-diode-array set at 280 nm, 360 and 520 nm using a reversed phase C-18 column (250×4.6 mm ID×5 µm; ACE). The amount of organic compounds, such as flavonoids and organic acid, in the extracts was determined using calibration curves of: quercetin, myricetin and trans-cinnamic acid.

HPLC-DAD/ESI-MS Analysis:

HPLC/MS analysis of the extract was performed using an HPLC (Thermo Finnigan surveyor), and interfaced to an LCQ ion trap spectrometer fitted with an electrospray interface (Thermo Finnigan, LCQ Advantage max). The elution program was the same as above, and the experiment was performed in both negative and positive modes. Spectra were scanned over a mass range of m/z 80-2000. The chromatogram shown in FIG. 1 shows that the organic compounds are well separated and fully identified by comparison of their relative molecular mass with that already described in the literature (E. Sousa de Brito et al., 2007 and L. Michodjehoun-Mestres et al., 2009).

TABLE 1

Quantitative Composition of Cashew Apple Extracts from Example 1 by HPLC at 280 nm

| | Compounds g/kg of CAE - Alcoholic | Compounds g/kg of CAE - Aqueous |
|---|---|---|
| Myricetin derivatives (A-F) (Expressed in terms of Myricetin) | 2.68 | 1.78 |
| Quercetin derivatives (G, H and J) (Expressed in terms of Quercetin) | 1.16 | 1.69 |
| 1-O-trans-cinnamoyl-beta-D-glucopyranose (I) (Expressed in terms of cinnamic acid) | 1.43 | 0.42 |

Example 2

Effect of Cashew Apple Extracts (CAE) on Body Weight and Fat Storage, Fatty Liver, Blood Glucose (Glycemia), Blood Insulin (Insulinemia), and Insulin Resistance Materials and Methods Five-week old C57BL/6NCrl mice (Charles River Laboratories, France) weighing around 20 g were used for the experiment. After 8 days of acclimation, mice were randomly assigned to the different experimental groups (9 animals per group) according to their fasted glycemia.

On Day 0, one group was kept under normal diet (23% of calories from proteins, 66% from carbohydrates, and 11% from fat) and the others were submitted to high fat diet (17% of calories from proteins, 28% from carbohydrates, and 55% from fat). The diets and water were provided ad libitum. The dosing formulations were administered by oral gavage every morning between 9 h and 10 h from Day 1 to Day 56. The dose volume was 10 ml/kg of body weight. The actual volume administered was calculated and adjusted based on the most recent body weight of each animal. The conditions tested were the followings:

Control Normal: Mice were fed a normal diet and were administered water once daily.

Control High Fat: Mice were fed a high fat diet and were administered water once daily.

CAE 200 mg/kg-Alcohol: Mice were fed a high fat diet and were administered Cashew Apple Extract obtained by hydro-alcoholic extraction once daily at the dose of 200 mg/kg of body weight.

CAE 200 mg/kg-Aqueous: Mice were fed a high fat diet and were administered Cashew Apple Extract obtained by aqueous extraction once daily at the dose of 200 mg/kg of body weight.

Figure 2:
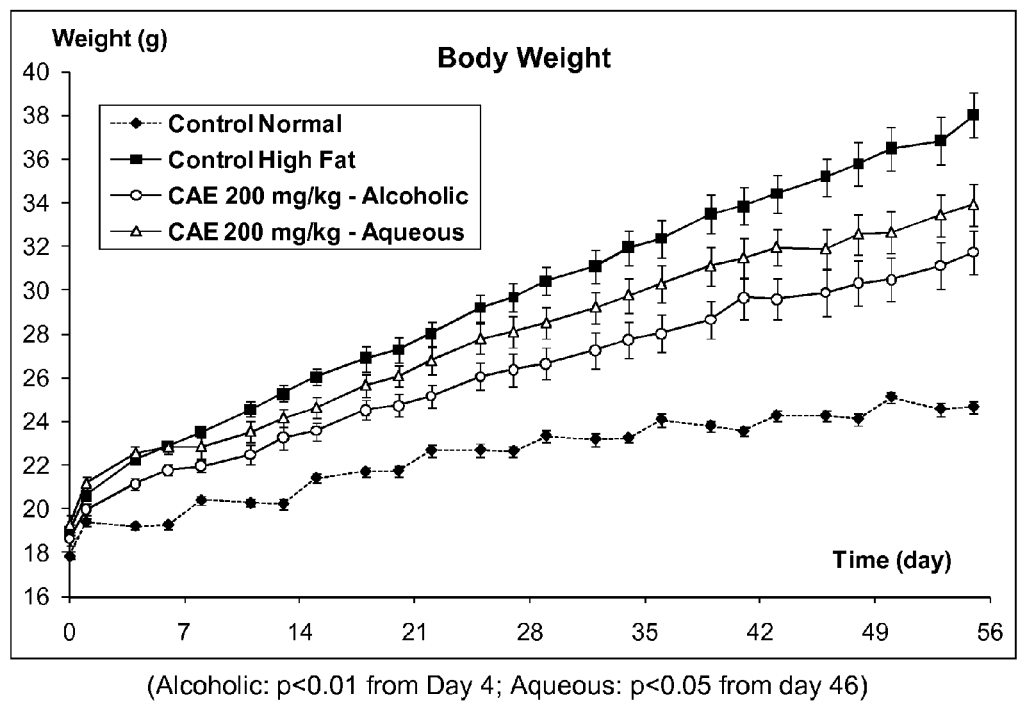
FIG. 2 shows the prevention effect of cashew apple extracts on body weight and fat storage in mouse submitted to high fat diet.
Figure 2:
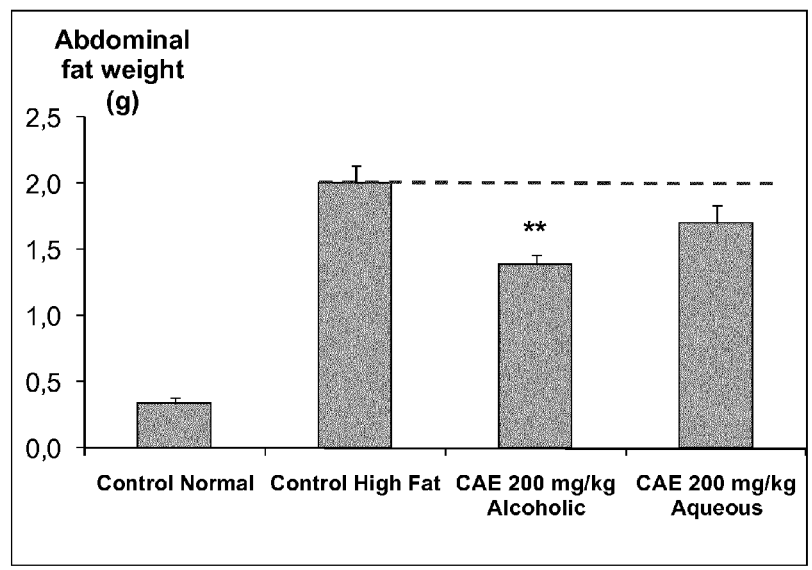
Figure 3:
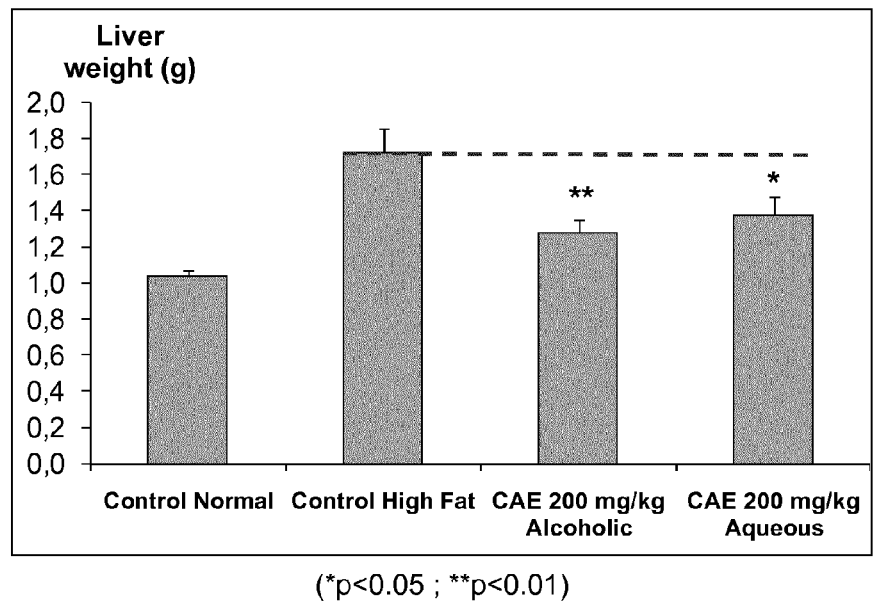
FIG. 3 shows the prevention effect of cashew apple extracts on fatty liver or hepatic steatosis in mouse submitted to high fat diet.
Figure 3:
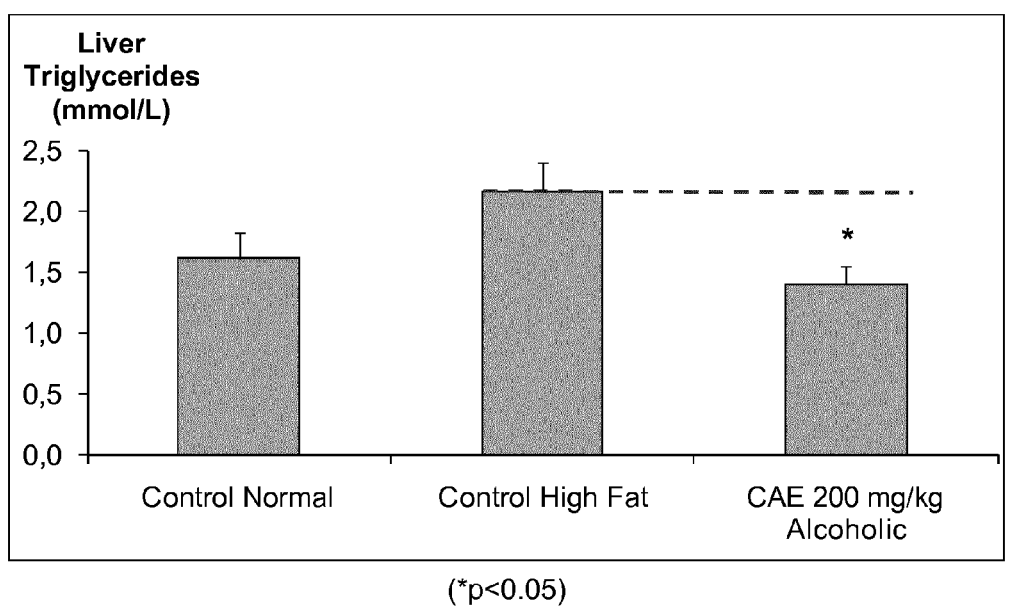
Figure 4:
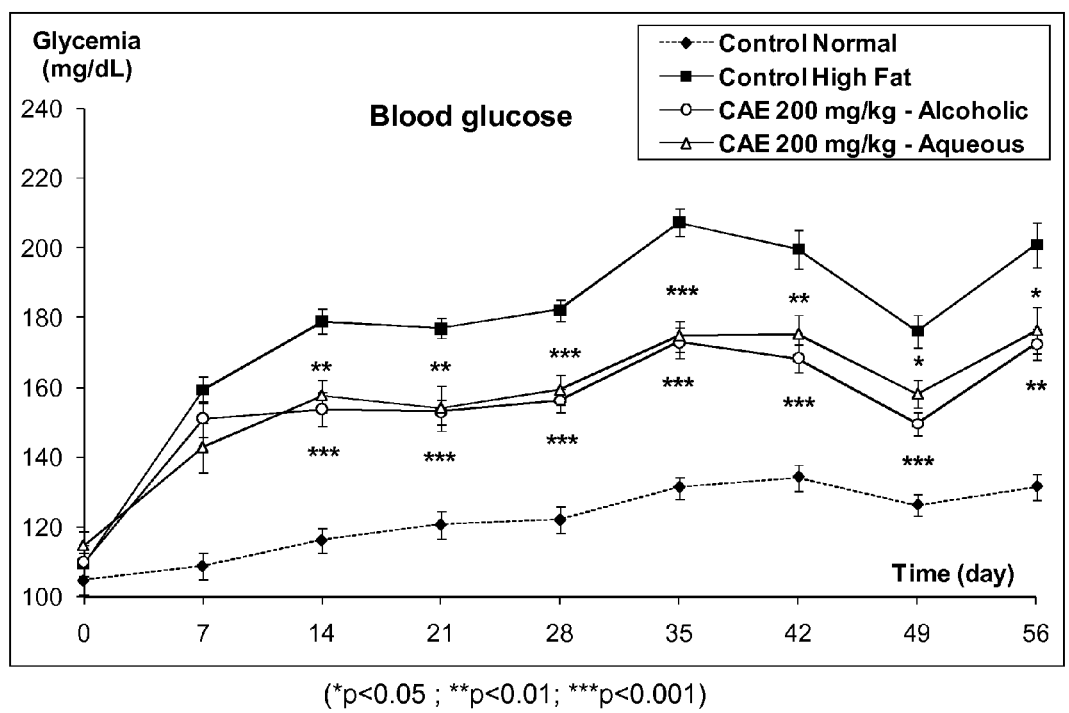
FIG. 4 shows the prevention effect of cashew apple extracts on blood glucose level in mouse submitted to high fat diet.
Figure 5:
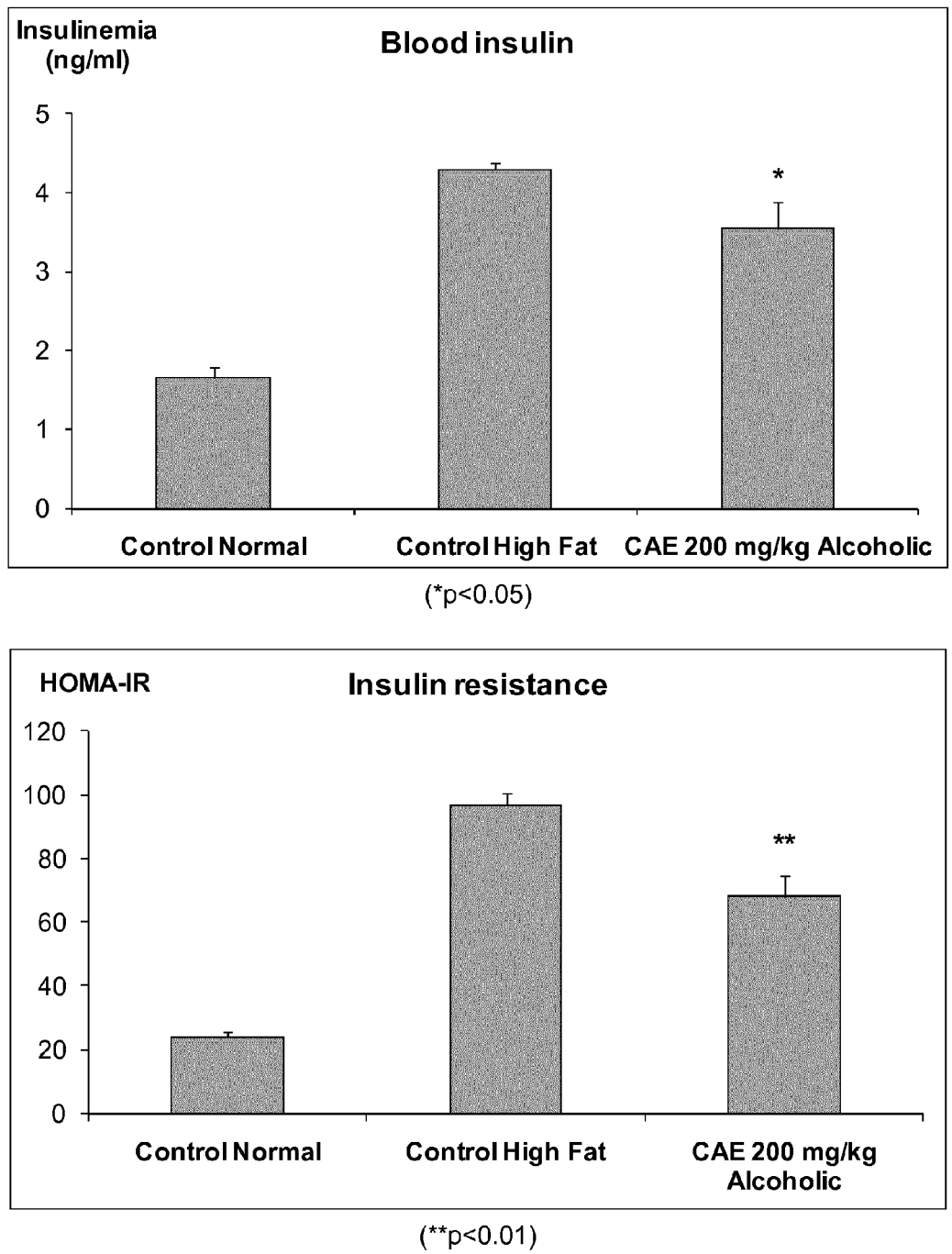
FIG. 5 presents the prevention effect of cashew apple extracts on blood insulin level and insulin resistance in mouse submitted to high fat diet.

The effect of cashew apple extracts on body weight and fat storage is shown on FIG. 2, on fatty liver on FIG. 3, on glycemia on FIG. 4, and on insulin and insulin resistance on FIG. 5.

Body weights of the mice were recorded at the arrival and then 3 times a week (on Monday, Wednesday, and Friday).

Fasting blood glucose levels were measured the day of randomization (Day 0) and on Day 7, 14, 21, 28, 35, 42, 49, and 56 between 13 h00 and 14 h00 on animals fasted for 4 hours. Whole blood samples (one drop) were collected via the tail vein for glucose determination using a hand-held glucometer (OneTouch Ultra 2, LifeScan).

At the end of the study, after a 4 hour fast, animals were anaesthetized by an intra peritoneal injection of 0.1 ml of Pentobarbital Sodium. A terminal blood sample was collected via cardiac puncture using heparin as anticoagulant. This terminal blood sampling conducts to the death of the animals. Blood samples were put at 4° C., centrifuged in the 30 min after collection; plasma harvested and kept frozen pending insulin analysis. The epididymal fat pad (abdominal fat) and the liver were harvested to measure their weights.

Liver triglyceride contents were measured using a commercial kit (TG PAP 150, Biomerieux, France) on 120 mg of liver grinded with an Ultra-Turrax grinder containing 1.2 ml NaCl 9 g/L-0.1% Triton X-100 at room temperature for 60 second.

Fasting plasma insulin levels were measured using an ELISA kit (Mercodia, Sweden). Then, insulin resistance indexes (HOMA-IR) were calculated using the formula: HOMA-IR=fasting insulin (mU/l)×fasting glucose (mmol/l)/22.5.

This protocol was approved by the Regional Ethic Committee (Montpellier, France)

Results

Body Weight and Abdominal Fat Weight (FIG. 2)

Mice submitted to high fat diet gained much more weight than those under normal diet. The difference of body weight is significant as soon as 4 days after the onset of the different diets ($p<0.05$). At the end of the study, after 8 weeks of diet, mice under high fat diet gained almost 3 times more weight than the control mice under regular diet. They reached 38±1 g, whereas mice under normal diet reached 24.6±0.3 g.

This increase of body weight induced by the diet is notably due to the storage of the energy in form of abdominal fat. Indeed, epididymal (abdominal) fat weights of mice under high fat diet were multiplied by 6 during the study compared to those of mice under normal diet: 2.01±0.13 and 0.34±0.05 g for high fat and normal diet, respectively. Perivisceral fat is recognized to be associated with or to be a strong risk factor of insulin resistance and metabolic syndrome.

CAE at the dose of 200 mg/kg of body weight reduced body weight gain induced by high fat diet. For hydro-alcoholic extract, this effect is significant from Day 4 of treatment and last all along the study ($p<0.01$ from Day 4). CAE decreased by half the effect of high fat diet on body weight gain, i.e. mice under high fat diet treated with CAE gained 13.1±1.09 g, whereas mice under high fat diet treated with water gained 19±0.92 g and mice under normal diet treated with water gained 6.8±0.32 g. Aqueous extract also reduced body weight gain of the mice in a less important manner.

This reduction is at least partly due to a reduction of fat storage in abdominal fat. Hydro-alcoholic CAE reduced by 31% fat storage into epididymal fat in mice submitted to high fat diet ($p<0.01$). Epididymal fat weight of CAE treated mice was 1.39±0.11 g, compared to 2.01±0.13 and 0.34±0.05 g for high fat diet control mice and normal diet control mice, respectively.

Liver Weight and Liver Triglycerides Content (FIG. 3)

High fat diet induced the storage of fat into the liver: what is called fatty liver or hepatic steatosis. The color of the liver became white instead of red for mice under normal diet and its weight was increased by 60%: 1.72±0.14 g for high fat diet versus 1.03±0.04 g for normal diet.

Either alcoholic or aqueous cashew apple extracts reduced significantly fatty liver: CAE-Alcoholic by 64% ($p<0.01$) and CAE-Aqueous by 49% ($p<0.05$)

This reduction of liver weight correlated with a significant reduction of liver triglycerides content ($p<0.05$).

Blood Glucose (FIG. 4)

After one week under diets (Day 7), fasting glycemia of mice submitted to high fat diet was significantly higher (159±3.9 mg/dL) than those of mice submitted to normal diet (109±3.6 mg/dL). Thereafter, this difference stayed rather constant all over the study.

Both, alcoholic and aqueous cashew apple extracts reduced by around 40% the glycemia of the pre-diabetic mice. This effect is clearly significant from Day 14 and lasted up to the end of the study (Day 56).

Blood Insulin and Insulin Resistance (FIG. 5)

Fasting insulinemia was also significantly increased by high fat diet, reaching 4.29±0.08 ng/ml compared to 1.65±0.14 ng/ml for mice under normal diet. In agreement with these increases in fasting glycemia and insulinemia induced by high fat diet, insulin resistance index (HOMA-IR) was multiplied by 4 showing that these animals are strongly insulin resistant.

At the end of the treatment period (Day 56), CAE reduced fasting blood insulin level induced by high fat diet ($p=0.05$). Insulinemia reached 3.54±0.35 and 4.29±0.08 ng/ml for CAE treated mice and control mice, respectively. Therefore, according to the HOMA-IR insulin resistance index, CAE reduced by 40% insulin resistance induced by high fat diet in pre-diabetic mice ($p<0.01$).

Conclusions

HDF induce a clear phenotype of metabolic syndrome in C57BL/6 mice with a significant increase in body weight gain, abdominal fat storage, fatty liver, fasting glycemia and insulinemia, and insulin resistance.

Alcoholic and aqueous cashew apple extracts at the dose of 200 mg/kg of body weight markedly reduced the defects induced by chronic consumption of high fat diet in mice. That comprises:

Reduction of body weight gain
Reduction of abdominal fat storage
Reduction of hepatic steatosis
Reduction of fasting glycemia
Reduction of fasting insulinemia
Reduction of insulin resistance Therefore, cashew apple extracts is shown to be a good ingredient to address one or several metabolic syndrome(s) and related defects.

Example 3

Curative Effect of Cashew Apple Extracts (CAE) on Body Weight, Fat Storage, Blood Glucose (Glycemia) and Blood Insulin (Insulinemia)

Materials and Methods

CAE-Alcoholic Extraction Process

Cashew apples (8 kg) are first crushed and pressed (hydraulic press) to remove the juice. The cake residue left (1.2 kg) is used for the following extraction processes. The freshly pressed cake (400 g) is extracted with about 4 L of 30% ethanol/water (V/V) for 2 hours at 50° C., under mechanical agitation. At the end of the extraction period, the solids are filtered out through a filter bag (PE-25) and 4 L of the liquid extract is removed.

The wet solids may be extracted one more time by stirring with another 2 volume of ethanol 30% for about 15 to 120 min further.

The solids are again filtered out and the obtained extracts were combined together, left for decantation and filtered through filter paper to remove non-soluble residues.

The clear supernatant obtained, was concentrated under reduced pressure to about 10% of its initial volume and the concentrated extract was freeze and lyophilized to obtain a yellow powder (20.5 g) of cashew apple.

Pharmacological Protocol

The protocol is comparable to Example 2 but the C57BL/6 mice were submitted to high fat diet for 4 weeks to induce obesity and pre-diabetes before the onset of the treatment with CAE. Then, hydro-alcoholic CAE were given for 4 weeks by oral gavage at the dose of 200 mg/kg of body Weight.

Results

Figure 6:
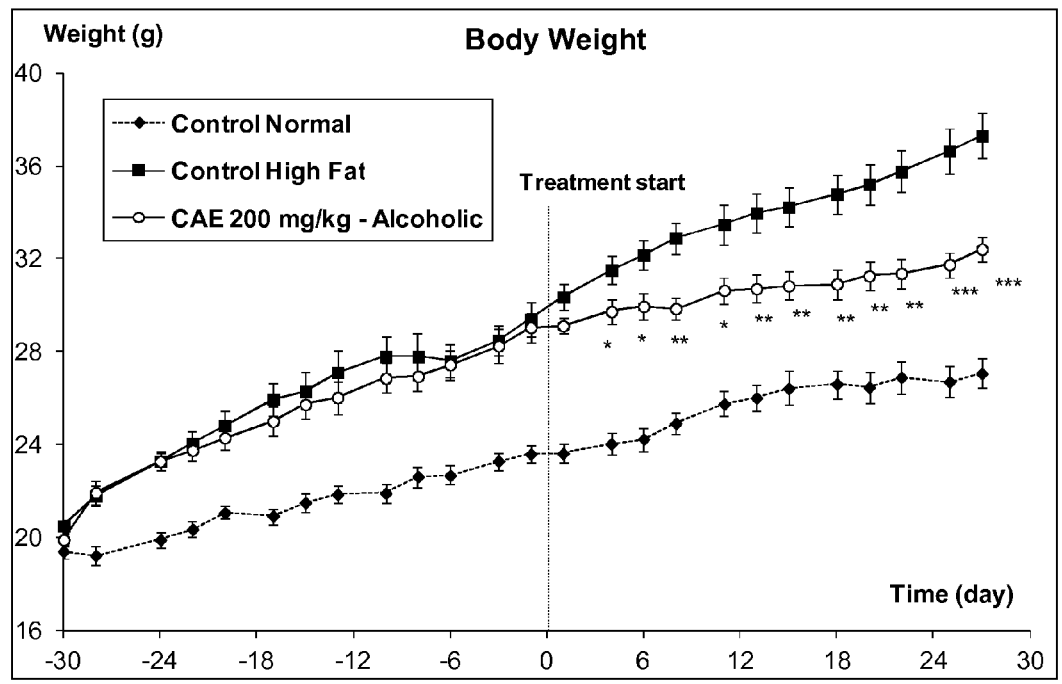
FIG. 6 presents the effect of cashew apple extracts on body weight and fat storage in pre-diabetic and obese mouse.
Figure 6:
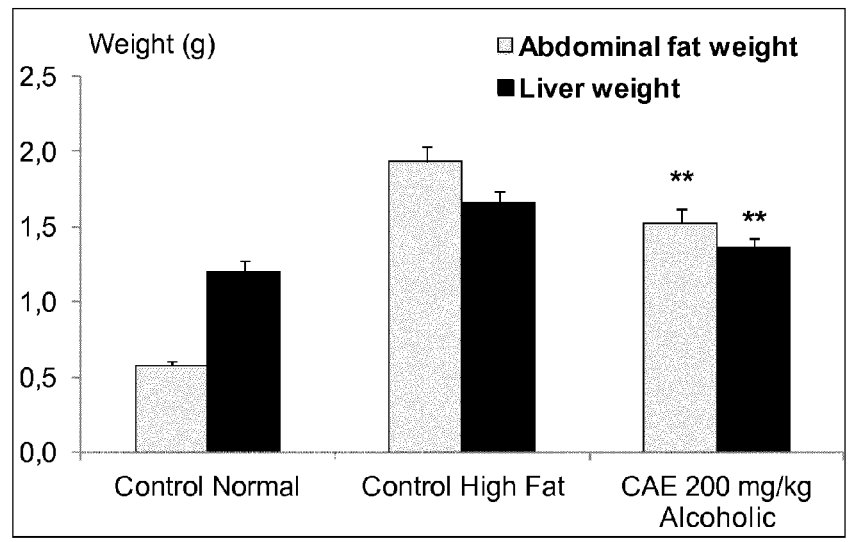

Effect on body weight and fat storage (FIG. 6)

After 4 weeks under diets, mice submitted to high fat diet presented a significant difference of body weight compared to mice submitted to normal diet ($p<0.001$) showing that obesity is well establish before the beginning of the treatment. They reached 30.4±0.5 g, whereas mice under normal diet reached 23.6±0.4 g.

As shown in FIG. 6, treatment with CAE at the dose of 200 mg/kg of body weight from Day 0 to Day 28 reduced body weight gain of the mice. This effect is significant from Day 4 of treatment and last all along the study (FIG. 6: *$p<0.05$; $p<0.01$; *$p<0.001$). At the end of the study, CAE treated mice reached 32.4±0.6 g, whereas water treated mice (placebo) reached 37.3±1 g: CAE treated mice gained 4.9 g less compared to control mice. This increase of body weight induced by the diet is notably due to the storage of the energy into abdominal fat. CAE reduced fat storage in the adipose tissue by 30.4% ($p<0.01$). Epididymal fat weight of CAE treated mice was 1.52±0.1 g, compared to 1.93±0.1 and 0.58±0.03 g for high fat diet control mice and normal diet control mice, respectively.

Fat was also stored into the liver leading to fatty liver disease (hepatic steatosis). CAE reduced fat storage in the liver by 65.2% ($p<0.01$). Liver weight of CAE treated mice was 1.36±0.06 g, compared to 1.66±0.07 and 1.20±0.07 g for high fat diet control mice and normal diet control mice, respectively.

Figure 7:
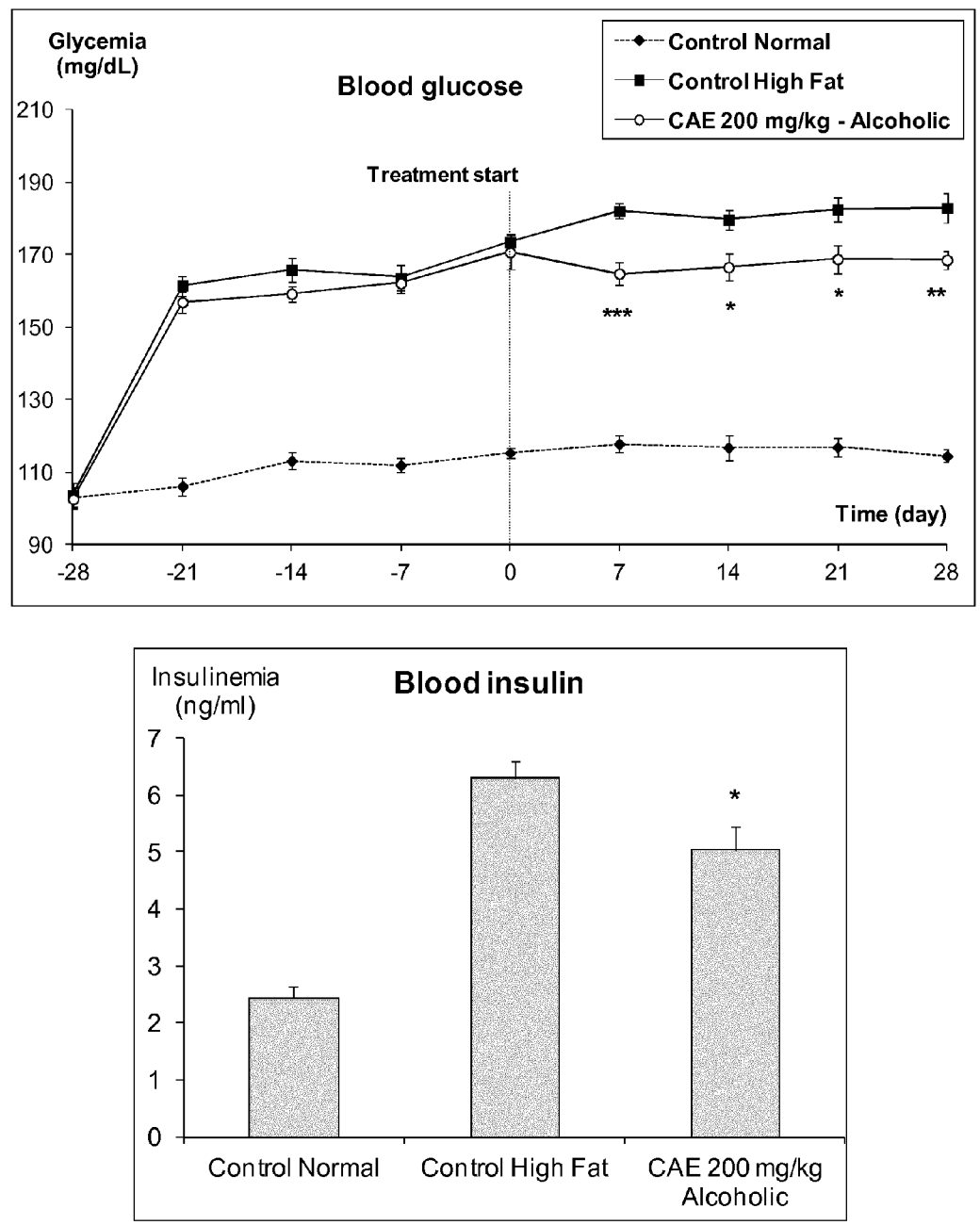
FIG. 7 presents the effect of cashew apple extracts on blood glucose level and blood insulin level in pre-diabetic and obese mouse.

Effect on Fasting Glycemia and Insulinemia (FIG. 7)

After four weeks under diets, fasting glycemia of mice submitted to high fat diet (173±1.5 mg/dL) was significantly higher ($p<0.001$) than those of mice submitted to normal diet (115±2.1 mg/dL). These results confirm the fact that mice under high fat diet were hyperglycemic at the onset of the treatment.

Cashew apple extracts reduced glycemia of the pre-diabetic mice by 22.7% in mean. This effect is clearly significant from the first week of treatment and lasted up to the end of the study (FIG. 7: *$p<0.05$; $p<0.01$; *$p<0.001$).

At the end of the treatment period, CAE also significantly reduced fasting blood insulin level ($p<0.05$). Insulinemia reached 5.03±0.43 and 6.30±0.29 ng/ml for CAE treated mice and control mice, respectively.

Conclusion

C57BL/6 mice submitted to high fat diet for 4 weeks became obese and pre-diabetic. Cashew apple extracts at the dose of 200 mg/kg of body weight markedly reduced these defects by reducing body weight gain, abdominal fat storage, hepatic steatosis, hyperglycemia, and hyperinsulinemia Therefore, cashew apple extracts appears to be a good ingredient to address obesity and pre-diabetes.

Example 4

Lipase Inhibition of Cashew Apple Extracts (CAE)

Materials and Methods

Lipase activity was assayed as follow: 25 μL of the solutions to be tested containing the inhibitors (cashew apple extracts) or distilled water (used as control) were added to 25 μL of the enzymatic solution consisting of 1 mg/mL of lipase from porcine pancreas (Sigma-Aldrich) in distilled water and pre-incubated during 5 min at room temperature. 50 μL of substrate solution, consisting of 0.1 mM 4-Methylumbelliferyl oleate (MUO; Sigma-Aldrich) in Dulbecco's phosphate buffer saline, was added and the mixture was incubated during 20 min at room temperature. The reaction was stopped by the addition of a solution of sodium citrate 100 mM and the luminofluorescence was read at 320 nm stimulation and 450 nm emission wavelengths. The assay was run in triplicates.

Results

Figure 8:
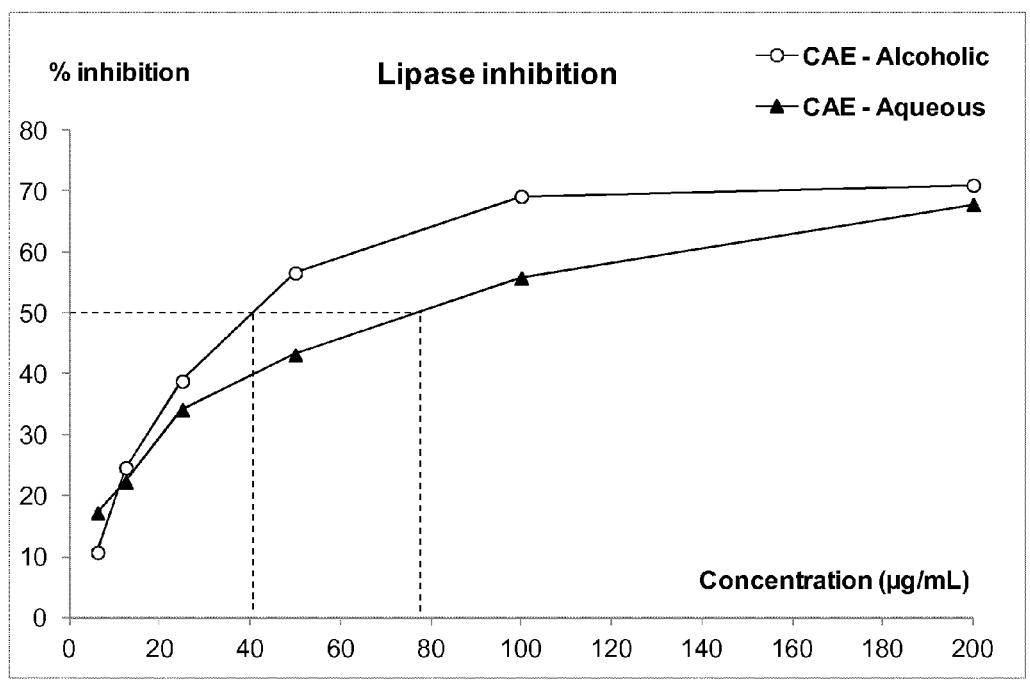
FIG. 8 presents the effect of cashew apple extracts on lipase inhibition.

As shown in FIG. 8, CAE inhibits lipase activity. The lipase inhibition activity of Alcoholic-CAE (IC50=41 μg/mL) is much higher compared to Aqueous-CAE (IC50=78 μg/mL).

Conclusion

CAE reduces risk factors of metabolic diseases, such as weight, fat storage, hepatic steatosis, glycemia, insulinemia, insulin resistance, at least in part by reducing fat digestion by inhibiting lipase activity. Alcoholic-CAE is more efficient to reduce lipase activity compared to Aqueous-CAE. That may also explain the higher effect observed with Alcoholic-CAE on body weight and fat storage compared to Aqueous-CAE (FIGS. 2 and 3).

Example 5

Thermal Degradation and Loss of Lipase Inhibition, Importance of 1-O-Trans-Cinnamoyl-Beta-D-Qlucoside for the Activity of Cashew Apple Extract (CAE)

Materials and Methods

The thermal degradation kinetics of CAE in water was investigated at 100° C. CAE was dissolved in deionised water at the concentration of 50 g/L and the solution was well homogenized. Volumes of 4 ml of this solution were placed in glass tubes, sealed, and placed in a mineral oil bath at 100° C. At predetermined intervals: 0, 10, 20, 30, 45, 60, 90, and 120 min, sample tubes were removed from the mineral oil bath and rapidly cooled in ice. For the analysis, 1 ml of each sample was mixed with 4 ml of HPLC grade methanol, homogenized, and filtrated on 0.45 μm HPLC filter. Then, 20 μL of the solution was analyzed in HPLC. The phytochemical composition of the samples was measured by reversed phase liquid chromatography using a C-18 column (ACE, 250×4.6 mm, 5 μm) at 280 nm. The areas under peak of the major components of CAE were measured in the different samples representing different time points of at 100° C.

Each sample was also assayed in the lipase inhibitory test by following the protocol described above in Example 4.

Results

Figure 9:
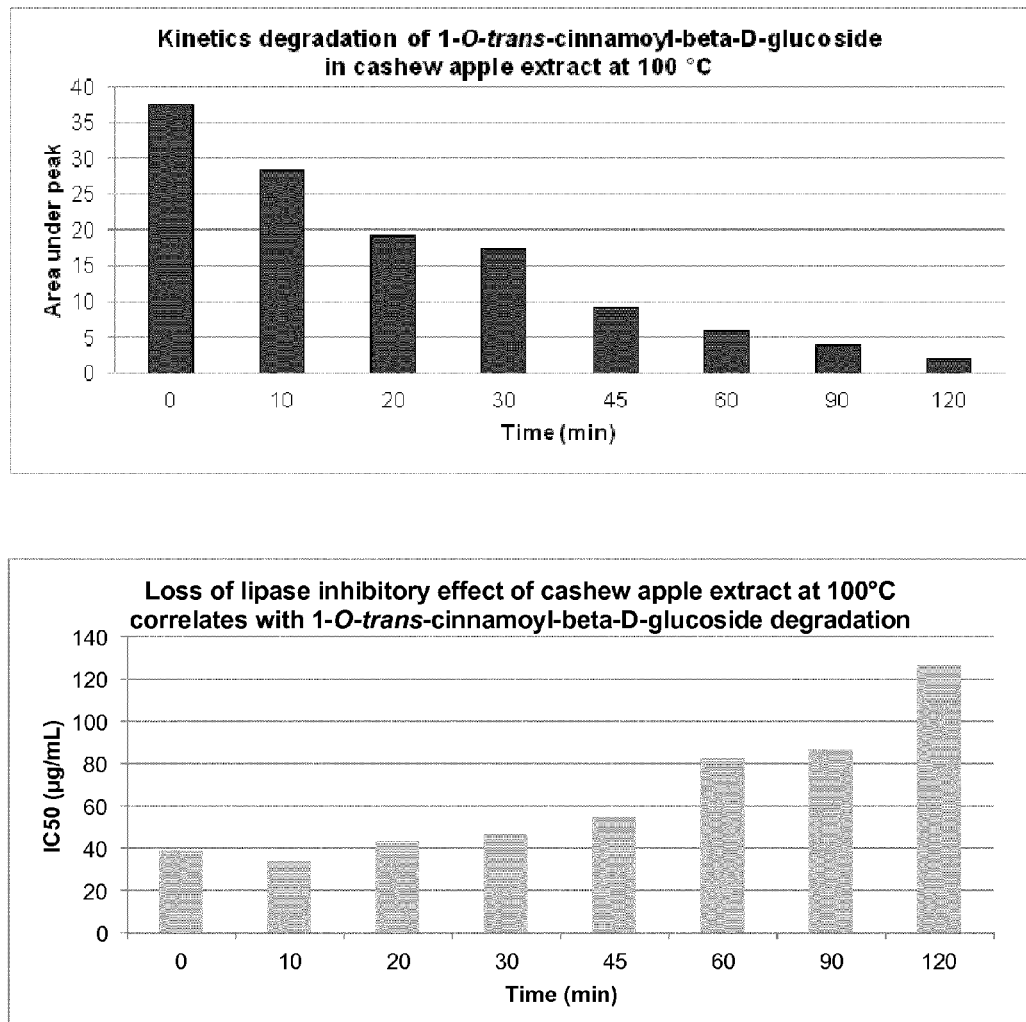
FIG. 9 shows the degradation with time of 1-O-trans-cinnamoyl-beta-D-glucopyranose (Compound I), in the cashew apple extract incubated at a temperature of 100° C., and the loss of lipase inhibition activity of the extract incubated for different times at 100° C.

As presented in FIG. 9 upper panel, the 1-O-trans-cinnamoyl-beta-D-glucoside compound of CAE was degraded by temperature. This degradation increased with the duration of the incubation. The amount of 1-O-trans-cinnamoyl-beta-D-glucoside was divided by 2 after 30 min of incubation at 100° C. and after 120 min of incubation this compound almost completely disappeared from the extract.

Regarding the corresponding lipase inhibition activity (FIG. 9, lower panel), we observed a complete correlation between lipase inhibition activity of CAE and the presence of unmodified 1-O-trans-cinnamoyl-beta-D-glucoside in the extract. The concentration to observe 50% of lipase inhibition (IC50) of CAE increased with the incubation time at 100° C., then, with the disappearance of 1-O-trans-cinnamoyl-beta-D-glucoside. After 60 min of incubation, CAE lipase inhibitory activity was divided by 2.

Conclusion

1-O-trans-cinnamoyl-beta-D-glucoside is one of the key components for CAE that is responsible of the inhibition of lipase activity and, by extension, of the reduction of risk factors of metabolic disease as demonstrated the mouse model.

The invention claimed is:

1. A dietary supplement, nutraceutical or food composition for reducing body weight when administered to a human in a diet as compared to a diet omitting the composition, said composition comprising an effective amount of a hydro-ethanolic cashew apple extract, wherein the extract comprises from 0.9 to 3.1 g/kg of cinnamic acid derivative, from 0.75 to 3 g/kg of quercetin derivative, and from 2 to 4.2 g/kg of myricetin derivative,
wherein the cinnamic acid derivative is 1-O-trans-cinnamoyl-beta-D-glucopyranose, the quercetin derivative is selected from the group consisting of quercetin 3-O-galactoside, quercetin 3-O-glucoside, and quercetin 3-O-rhamnoside, and the myricetin derivative is selected from the group consisting of myricetin 3-O-galactoside, myricetin 3-O-glucoside, myricetin 3-O-xylo-pyranoside, myricetin 3-O-arabino-pyranoside, myricetin 3-O-arabinofuranoside and myricetin 3-O-rhamnoside.

2. The composition according to claim 1, wherein the cashew apple extract comprises a total phenol content ranging from 3 to 7% by weight compared to the total weight of the extract.

3. The composition according to claim 1, wherein the cashew apple extract is prepared by the following steps:
a) contacting crushed and pressed cashew apples with 2 to 20 times their weight of a first extraction solvent consisting of water and ethanol, stirring, filtering out wet solids and collecting the first extraction solvent at a temperature above 35° C.,
b) washing the wet solids by stirring with a second extraction solvent consisting of water and ethanol,
c) filtering the wet solids and collecting the second extraction solvent,
d) combining the first and second extraction solvents and removing non-soluble residues,
e) evaporating the combined first and second extraction solvents, and
f) recovering a dry extract.

4. The composition according to claim 1, further comprising a carrier.

5. The composition according to claim 1, wherein the composition is a dietary supplement composition, and wherein the cashew apple extract is in an amount ranging from 1% to 100% by weight compared to the total weight of the dietary supplement composition.

6. The composition according to claim 1, wherein the composition is a nutritional or food composition, and wherein the cashew apple extract is in an amount ranging from 0.1 to 5% by weight compared to the total weight of the nutraceutical or food composition.

7. The composition according to claim 1, wherein the cashew apple extract inhibits lipase activity.

8. A dietary supplement, nutraceutical or food composition for reducing body weight when administered to a human in a diet as compared to a diet omitting the composition, said composition comprising an effective amount of a cashew apple extract comprising cinnamic acid derivatives, quercetin derivatives, and myricetin derivatives, wherein the total amount of cinnamic acid derivatives, quercetin derivatives, and myricetin derivatives is of at least 2 g/kg of the extract, and wherein the cinnamic acid derivative is 1-O-trans-cinnamoyl-beta-D-glucopyranose, the quercetin derivative is selected from the group consisting of quercetin 3-O-galactoside, quercetin 3-O-glucoside, and quercetin 3-O-rhamnoside, and the myricetin derivative is selected from the group consisting of myricetin 3-O-galactoside, myricetin 3-O-glucoside, myricetin 3-O-xylo-pyranoside, myricetin 3-O-arabinopyranoside, myricetin, 3-O-arabinofuranoside and myricetin 3-O-rhamnoside.

9. A dietary supplement, nutraceutical or food composition for reducing body weight when administered to a human in a diet as compared to a diet omitting the composition, said composition comprising an effective amount of a hydro-ethanolic cashew apple extract, wherein the extract comprises from 1.7 to 4g/kg of myricetin derivative, from 1.5 to 2.5 g/kg of quercetin derivative, and from 0.4 to 2 g/kg of cinnamic acid derivative, wherein the cinnamic acid derivative is 1-1-O-trans-cinnamoyl-beta-D-glucopyranose, the quercetin derivative is selected from the group consisting of quercetin 3-O-galactoside, quercetin 3-O-glucoside, and quercetin 3-O-rhamnoside, and the myricetin derivative is selected from the group consisting of myricetin 3-O-galactoside, myricetin 3-O-glucoside, myricetin 3-O-xylo-pyranoside, myricetin 3-O-arabinopyranoside, myricetin 3-O-arabinofuranoside and myricetin 3-O-rhamnoside.

10. A method for reducing body weight or limiting body weight gain in a subject in need thereof comprising:
administering a therapeutically effective amount of the composition according to claim 1 to the subject.

11. The method according to claim 10, wherein the method reduces or controls the body weight of the subject.

12. A method for extracting cashew apple comprising:
a) contacting cashew apples with 2 to 20 times their weight of a first extraction solvent consisting of water and ethanol at a temperature above 35° C.,
b) filtering out wet solids and collecting the first extraction solvent,
c) washing the wet solids by stirring with a second extraction solvent consisting of water and ethanol,
d) filtering out the wet solids and collecting the second extraction solvent,
e) combining the first and second extraction solvents and removing non-soluble residues,
f) evaporating the combined first and second extraction solvents, and
g) recovering a dry extract.

* * * * *